United States Patent [19]

Alfs et al.

[11] 4,236,033
[45] Nov. 25, 1980

[54] PROCESS FOR THE MANUFACTURE OF P-ALKYLPHENOLS

[75] Inventors: Helmut Alfs; George Boehm; Heinz Steiner, all of Marl, Fed. Rep. of Germany

[73] Assignee: Chemische Werke Huels Aktiengesellschaft, Marl, Fed. Rep. of Germany

[21] Appl. No.: 948,609

[22] Filed: Oct. 4, 1978

[30] Foreign Application Priority Data

Nov. 10, 1977 [DE] Fed. Rep. of Germany ....... 2745589

[51] Int. Cl.³ .............................................. C07C 37/14
[52] U.S. Cl. .................................... 568/793; 568/788
[58] Field of Search ........................ 568/790, 793, 788

[56] References Cited

U.S. PATENT DOCUMENTS

| | | | |
|---|---|---|---|
| 3,257,467 | 6/1966 | O'Neill et al. | 568/793 |
| 3,278,463 | 10/1966 | O'Neill et al. | 568/793 |
| 3,308,168 | 3/1967 | O'Neill et al. | 568/793 |
| 3,422,157 | 1/1969 | Kaufman et al. | 568/793 |

FOREIGN PATENT DOCUMENTS

| | | |
|---|---|---|
| 259106 | 5/1963 | Australia . |
| 1443346 | 10/1973 | Fed. Rep. of Germany . |
| 2526644 | 12/1976 | Fed. Rep. of Germany . |
| 953929 | 4/1964 | United Kingdom ..................... 568/793 |

OTHER PUBLICATIONS

Ullmanns Encyclopedia of Industrial Chemistry, vol. 13, pp. 440 to 447 (1962).

*Primary Examiner*—Werren B. Lone
*Attorney, Agent, or Firm*—Millen & White

[57] ABSTRACT

In a process for the manufacture of a p-alkylphenol by alkylating phenol with an olefin of 3 to 4 carbon atoms, at an elevated temperature, in the liquid phase, in two reaction zones in series and in the presence of a strongly acidic ion exchange resin as the catalyst, an improvement comprises:

(a) passing in a first reaction stage at a temperature of 80°–140° C. over a suspended catalyst, the olefin as a gas at a gas velocity of 30 to 20 cm/second, based on the free cross-section of the empty reactor and on a molar volume of 25 liters per mole of olefin, from below into the reaction mixture; and (b) passing the resulting liquid reaction product, into a second reaction stage, at a temperature of 80°–140° C. over a fixed-bed catalyst;

wherein a catalyst having an exchange capacity of 70–120 m. equivalents/100 cm³ is used in both reaction stages.

10 Claims, No Drawings

PROCESS FOR THE MANUFACTURE OF P-ALKYLPHENOLS

BACKGROUND OF THE INVENTION

The present invention relates to a process for the manufacture of p-alkylphenols by alkylating phenol with olefins of 3 to 4 carbon atoms, at elevated temperatures, in the liquid phase, in two reaction zones in series and in the presence of strongly acidic ion exchange resins as the catalyst.

It is known to alkylate phenol with olefins in the presence of protonic acids or Lewis acids, such as sulphuric acid or boron trifluoride, respectively. Unfortunately, the use of such catalysts necessitates, for example, the use of corrosion resistant installations. Furthermore, the resulting products cannot be obtained with the necessary purity or with the desired color quality.

Recently, therefore, strongly acidic ion exchange resins in the H-form, especially sulphonated ion exchange resins, such as sulphonated ion exchange resins based on phenol-formaldehyde resins or polystyrene resins, have also been employed as fixed-bed catalysts for alkylation. Although high space-time yields are obtained, local over-heating in the strongly exothermic reaction cannot be reliably excluded. As a result, impure, and, in particular, discolored alkylphenols are formed which are unsuitable for further use. Moreover, the ion exchange resins are damaged.

In the process of DT-OS No. 1,443,346 (equivalent to Australian PS No. 259,106), local overheating is prevented by circulating the reaction mixture, consisting of olefins and phenols and the alkylphenols formed, via a heat exchanger through the reactor and only partially alkylating it. Subsequently, an amount corresponding to the fresh feed of olefins and phenols is withdrawn and the mixture is reacted further in a second stage. A disadvantage of this process is the expenditure required to circulate the reactants and to heat them, which results in decomposition or discoloration of the end products. Moreover, only low space-time yields can be achieved by this process.

According to U.S. Pat. No. 3,257,467, phenols are alkylated with olefins in a single reaction stage, in the presence of strongly acidic ion exchange resins, in a heat-insulated reactor. The catalyst is easily prematurely damaged by local overheating. This process, furthermore, is capable of achieving only space-time yields which are, again, unsatisfactory.

In the process of DT-OS No. 2,526,644, the reaction is carried out using a cation exchanger which has a particle size of 100 to 200 micrometers and is suspended in the liquid reaction mixture. Although, as expected, the removal of the heat of reaction is better with this process, the process is not satisfactory with respect to the yield of the desired p-alkyl compound.

All the processes, however, have the common disadvantage that the alkylphenols formed tend, during the subsequent working-up of the reaction products by distillation, to redissociate into the starting compounds, presumably because of impurities originating from the catalyst. As a result of this, not only is the yield reduced but, especially when readily volatile olefins are formed, such severe vacuum irregularities can be caused in the distillation section that working-up is made very considerably more difficult.

SUMMARY OF THE INVENTION

Accordingly, it is an object of this invention to provide a process for the manufacture of p-alkylphenols from olefins of 3 to 4 carbon atoms and phenol, which enables a qualitatively high-grade p-alkylphenol product, which can be further worked-up without difficulty, to be manufactured with high selectivity and high space-time yields and, moreover, which avoids the difficulties of the prior art processes.

Upon further study of the specification and appended claims, further objects and advantages of this invention will become apparent to those skilled in the art.

These objects have been achieved by providing in a process for the manufacture of a p-alkylphenol by alkylating phenol with an olefin of 3 to 4 carbon atoms, at an elevated temperature, in the liquid phase, in two reaction zones in series and in the presence of a strongly acidic ion exchange resin as the catalyst, the improvement which comprises (a) passing in a first reaction stage at a temperature of 80°–140° C. over a suspended catalyst, the olefin as a gas at a gas velocity of 3 to 20 cm/second, based on the free cross-section of the empty reactor and on a molar volume of 25 liters per mole of olefin, from below into the reaction mixture; and (b) passing the resulting liquid reaction product, into a second reaction stage, at a temperature of 80°–140° C. over a fixed-bed catalyst;

wherein a catalyst having an exchange capacity of 70–120 m. equivalents/100 cm$^3$ is used in both reaction stages.

DETAILED DISCUSSION

In the first reaction stage, the olefin is passed, as a gas, from below into the reaction mixture through a frit, a sieve plate or another suitable distributing device. By this means, intensive mixing of the contents of the reactor is achieved and the catalyst is kept in suspension. The gas should be passed into the reactor at a gas velocity of about 3–20 cm/second, based on the free cross-section of the empty reactor and on a molar volume of 25 liters per mole of olefin. Below 3 cm/second, the proportion of m-alkylphenol increases greatly and above 20 cm/second troublesome plate bubbles are likely to arise in the reaction mixture. It is, however, advisable to work with gas velocities which are as high as possible. Preferred velocities are 5–15 cm/second, especially 8–12 cm/second. Typical reactant flow rates are, for phenol 0.15–5000 kg/hour and for olefin 0.025–500 m$^3$/hour.

The reaction in the first stage is carried out at a temperature of 80° to 140° C. A temperature range of 100° to 120° C. is preferred because this range is particularly advantageous from the points of view of desirable rates of reaction and low formation of by-products. Below 80° 1 C., the formation of by-product takes place to an increased extent and above 140° C. there is an increased possibility of the catalyst being damaged by heat.

Suitable catalysts include the conventional organic sulphonated cation exchangers, for example, sulphonated phenolformaldehyde or benzene-formaldehyde resins, sulphonated cross-linked styrene polymers and, particularly advantageously, sulphonated polystyrene-divinylbenzene resins. The resins can have a gel-type structure, but macroreticular (macroporous) resins are preferred. The particle size of the catalyst has no influence on the reaction, provided, of course, that the catalyst reaches the suspended state at the indicated gas velocities. This is the case with the customary catalysts available commercially, which usually have particle sizes of 0.3 to 1 mm. If catalysts with a larger particle size are to be used, a simple routine preliminary experiment must be carried out to determine whether the catalyst will reach the suspended state.

The exchange resins are used in the acid form in the dry state. If commercially available acidic ion exchange resins which have an exchange capacity of 130 to 180 m. equivalents/100 cm$^3$ (measured in the water-moist state) are used, a strong tendency to redissociate into the starting compounds is found when the reaction product is worked up by distillation. Surprisingly, it has now been found that when weakened ion exchangers are used, which have a capacity of only 70 to 120 m. equvalents/100 cm$^3$, preferably 80–100 m. equivalents/100 cm$^3$, and in particular about 110 m. equivalents/100 cm$^3$, this tendency to redissociate virtually disappears. Below 70 m. equivalents/100 cm$^3$, the economics of the process deteriorate noticeably and there is increased formation of by-product.

These weakened catalysts can be produced by treating the fresh, water-moist ion exchange resins with amounts of salts, such as aluminum sulphate, zinc sulphate, tin sulphate and the like sufficient to lower the capacity to the required range. They are then washed until neutral and dried. Drying is advantageously carried out by removing the water cyclically as an azeotrope with an entrainer, such as benzene, cyclohexene, toluene and the like. A residual moisture content in the catalyst should be less then 0.5% of water, since, as is known, a water-containing catalyst has a reduced catalytic activity.

The reaction is appropriately carried out using an excess of phenol. It is also possible to carry out the reaction with stoichiometric amounts of reactants. In this case, undesirably high proportions of dialkylphenols form. The molar ratio of phenol:olefin used in practice is approximately between 1.3:1 and 3:1. With a molar ratio above 3:1, there is hardly an additional action and increased costs are merely incurred for distillation of the excess phenol. A particularly advantageous molar ratio is about 2:1. Normally, 25–250 g of exchange resin in the first stage and 50–500 g in the second stage are employed per kg of phenol used as starting material in the first step.

The reaction can also be carried out using a conventional solvent, e.g. octane, nonane or decane.

The process can be carried out under any desired pressure, provided that the olefin remains in the gaseous form. However, normal pressure or a slight excess pressure which suffices to overcome the flow resistances is preferred. Typical pressures are 1.0–10 atm.

After separating off the catalyst, the product from the first process stage passes into the second process stage. The catalyst can be separated off by filter candles, filter plates and the like in the first process stage. It is also possible to build the reactor so high that a calmed catalyst-free liquid zone, from which the catalyst-free product can be withdrawn, arises above the catalyst zone. In the second reaction zone, which is operated at a temperature of 80°–140° C., preferably 100°–120° C., and especially 120° C., the product from the first reaction stage is subjected to a subsequent reaction on a fixed-bed catalyst of an exchange capacity in the same range as specified for the first stage. Preferably the second stage catalyst has the same capacity as the first stage catalyst.

This second stage converts the proportion of o-alkyl- and 2,4-dialkyl-phenol, which in any case is very small, into the desired p-alkylphenol.

The residence time in the second reaction zone should preferably be about 0.5 to 2 hours, and in the first reaction zone a residence time of 1 to 3 hours is preferred. However, longer reaction times have no adverse effect on the product spectrum.

Except as indicated herein, the process is carried out under conventional conditions as described, e.g., in the Australian PS No. 259,106, whose disclosure is incorporated by reference herein.

The p-alkylphenols manufactured by the process of this invention are valuable starting materials for the manufacture of stabilizers, anti-aging agents, pharmaceuticals and the like. In this context also see, for example, Kirk-Othmer, Encyclopedia of Chemical Technology, 2nd edition, Volume 1 901 to 916, or Ullmanns Encyclopädie der Technischen Chemie (Ullmanns Encyclopedia of Industrial Chemistry), Volume 13, 440 to 447 (1962).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

This example demonstrates the influence of the gas velocity in the first reaction zone.

92 g of a dry, macroporous exchange resin with a capacity of 110 m. equivalents/100 cm$^3$ are filled into a reactor with an internal diameter of 3 cm and a height of 100 cm. The catalyst has a particle size of 0.3 to 1 mm. The reactor is filled with phenol and then different amounts of phenol and isobutylene are added as indicated in Table 1, at a reaction temperature of 115° C., through a glass frit located in the base of the reactor. After the steady state was reached, the products withdrawn at the top of the reactor (experiments a to c) had the compositions shown in Table 1 (calculated phenol-free). An additional experiment (d) using a higher gas velocity was carried out at the same reaction temperature and with the same catalyst in a reactor which had an internal diameter of 70 cm and a height of 450 cm and contained 200 kg of exchange resin. The results are also listed in Table 1.

TABLE

|  | EXPERIMENT | | | |
|---|---|---|---|---|
|  | a (comparative) | b (comparative) | c | d |
| Anount of phenol added, kg/hour | 0.15 | 0.3 | 0.45 | 2,000 |
| Amount of isobutylene added, m$^3$/hour | 0.025 | 0.05 | 0.075 | 205 |
| Gas velocity, cm/second | 1 | 2 | 3 | 15 |
| Content, in % by weight of |  |  |  |  |
| o-tert-butylphenol | 1.8 | 3.0 | 3.7 | 2.4 |
| m-tert-butylphenol | 15.9 | 4.9 | 1.0 | <0.2 |
| p-tert-butylphenol | 75.4 | 84.0 | 85.3 | 93.9 |
| 2,4-ditert-butylphenol | 6.9 | 8.1 | 9.9 | 3.5 |

EXAMPLES 2-7

Per hour, 450 g. of phenol and 75 liters of isobutylene are introduced, through a frit in the base of the reactor, into a glass reactor (first reaction stage) which has an internal diameter of 3 cm and a height of 100 cm. The reactor is filled with 92 g of macroporous cation exchanger having an exchange capacity as listed in Table 2. The gas velocity for the isobutylene is 3 cm/second; the reaction temperature is between 80° and 130° C.; and the molar ratio of phenol: isobutylene is 1.9:1.

The product (a mixture of unconverted phenol, o-tert-,m-tert- and p-tert-butylphenol and 2,4-ditert-butylphenol) which issues from the glass reactor is passed through a second reactor (second reaction stage), which has an internal diameter of 5 cm and a length of 50 cm and in which 350 g of a macroporous catalyst are arranged in a fixed bed.

The product which issues from this reactor can be worked-up by distillation without any after-treatment.

The results are shown in Table 2.

TABLE 2

| EXAMPLE | REACTION STAGE | REACTION TEMPERATURE [°C.] | ACTIVITY OF THE CATALYST [m. equivalents/100 cm$^3$] | GAS VELOCITY [cm/second] | ortho-tert-butyl-phenol [%] | meta-tert-butyl-phenol [%] | para-tert-butyl-phenol [%] | di-tert-butyl-phenol [%] |
|---|---|---|---|---|---|---|---|---|
| 2 | I | 115 | 100 | 3 | 7.0 | 0.7 | 80.5 | 11.8 |
|   | II | 115 | 100 | 3 | 2.5 | 0.7 | 91.6 | 5.2 |
| 3 | I | 115 | 90 | 3 | 11.2 | 0.5 | 70.8 | 17.5 |
|   | II | 115 | 90 | 3 | 3.0 | 0.5 | 87.8 | 8.7 |
| 4 | I | 115 | 80 | 3 | 15.3 | 0.2 | 61.3 | 23.2 |
|   | II | 115 | 80 | 3 | 4.3 | 0.2 | 85.4 | 10.1 |
| 5 | I | 80 | 110 | 3 | 7.0 | 0.2 | 77.6 | 15.2 |
|   | II | 80 | 110 | 3 | 2.3 | 0.2 | 85.1 | 12.4 |
| 6 | I | 100 | 110 | 3 | 3.7 | 1.1 | 83.3 | 11.9 |
|   | II | 100 | 110 | 3 | 1.8 | 1.1 | 92.2 | 4.9 |
| 7 | I | 130 | 110 | 3 | 3.0 | 4.9 | 84.0 | 8.1 |
|   | II | 130 | 110 | 3 | 1.6 | 4.9 | 89.3 | 4.2 |

EXAMPLES 8 and 9

These examples demonstrate the improvement which is evident when the product manufactured according to the invention is worked-up by distillation.

Analogously to Examples 2 to 7, the alkylation is carried out at a temperature of 115° C. in the first stage and of 120° C. in the second stage. In Example 8, catalysts with an exchange capacity of 110 m. equivalents/100 cm$^3$ are used in each stage (according to the invention) and in Example 9, the reaction is carried out in accordance with the state of the art using catalyst with an exchange capacity of 140 m. equivalents/100 cm$^3$.

The products obtained in each case are worked-up by distillation. The distillation column used is a packed column with a diameter of 60 mm and a height of 1 m. The distillation is carried out under a pressure of 33 m bars. The isobutylene split off is condensed in a receiver, which is cooled to −78° C., and then weighed.

The results can be seen by inspection of Table 3.

TABLE 3

| EXAMPLE | ISOBUTYLENE SPLIT OFF DURING THE DISTILLATION, BASED ON 100 g OF REACTION PRODUCT [%] | SOLIDIFICATION POINT OF THE PURE PRODUCT OBTAINED*[C.] | GAS CHROMATOGRAM OF THE PURE PRODUCT | | | | |
|---|---|---|---|---|---|---|---|
| | | | phenol | o-tert-butylphenol [%] | m-tert-butylphenol [%] | p-tert-butylphenol [%] | 2,4-di-tert butylphenol [%] |
| 8 | 0.4 | 98.7 | 0.01 | 0.43 | 0.13 | 98.94 | 0.49 |
| 9 (comparative) | 4.9 | 81.8 | 9.6 | 2.4 | 0.51 | 86.92 | 0.57 |

*Solidification point of pure p-tert-butylphenol: 98.9° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the manufacture of a p-alkylphenol comprising alkylating phenol with an olefin of 3 to 4 carbon atoms at an elevated temperature in the liquid phase in two reaction zones in series, in the presence of a strongly acidic ion exchange resin of an exchange capacity of 70 to 120 m. equivalents/100 cm$^3$, as the catalyst, in the first reaction stage at a temperature of 80°–140° C., and at a gas velocity of 3 to 20 cm/second, based on the free cross-section of the empty reactor and on a molar volume of 25 liters per mole of olefin.

2. The process of claim 1, wherein the liquid reaction product from the first zone is passed into the second reaction zone and the reaction in the second zone is effected at a temperature of 80°–140° C.

3. The process of claim 2, wherein the catalyst in the first zone is a suspended catalyst and the catalyst in the second zone is a fixed-bed catalyst.

4. The process of claim 2, wherein the olefin gas is passed into the first zone from below into the reaction mixture.

5. The process of claim 2, wherein the temperature in the first reaction zone is 100°–120° C. and the temperature in the second reaction zone is about 120° C.

6. The process of claim 1, wherein the exchange capacity of the catalyst is about 110 m.equivalents/100 cm$^3$.

7. The process of claim 5, wherein the exchange capacity of the catalyst is about 110 m.equivalents/100 cm$^3$.

8. The process of claim 2, wherein the exchange capacities of the catalyst in each stage are the same.

9. The process of claim 1, wherein the exchange capacity of the catalyst is 80–100 m.equivalent/100 cm$^3$.

10. In a process for the manufacture of a p-alkylphenol by alkylating phenol with an olefin of 3 to 4 carbon atoms, at an elevated temperature, in the liquid phase, in two reaction zones in series, the improvement which comprises passing, in the first reaction stage at a temperature of 80°–140° C., the olefin over the catalyst, as a gas at a gas velocity of 3 to 20 cm/second, based on the free cross-section of the empty reactor and on a molar volume of 25 liters per mole of olefin;

and the catalyst in both stages is an acidic ion exchange resin whose ion exchange capacity is selected at a value which maximizes the yield of alkylphenol.

* * * * *